(12) United States Patent
Waldman et al.

(10) Patent No.: US 8,900,632 B2
(45) Date of Patent: Dec. 2, 2014

(54) RAPIDLY DISINTEGRATING COATED TABLETS

(71) Applicant: McNeil-PPC, Inc., Skillman, NJ (US)

(72) Inventors: Joel H. Waldman, Chalfont, PA (US);
Anthony S. Bean, Harleysville, PA (US); Fernanda Franzoi, Sao Jose' dos Campos-Sao Paulo (BR)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/757,206

(22) Filed: Feb. 1, 2013

(65) Prior Publication Data

US 2013/0202700 A1    Aug. 8, 2013

Related U.S. Application Data

(60) Provisional application No. 61/595,767, filed on Feb. 7, 2012.

(51) Int. Cl.
*A61K 9/28* (2006.01)
*A61K 9/20* (2006.01)
*A61K 31/167* (2006.01)
*A61J 3/10* (2006.01)

(52) U.S. Cl.
CPC ............ *A61K 9/2072* (2013.01); *A61K 9/2866* (2013.01); *A61K 31/167* (2013.01); *A61K 9/2893* (2013.01)
USPC ............................ 424/467; 424/474; 424/480

(58) Field of Classification Search
USPC ......................................... 424/467, 474, 480
See application file for complete search history.

(56) References Cited

U.S. PATENT DOCUMENTS

| | | |
|---|---|---|
| 4,279,926 A | 7/1981 | Bruzzese et al. |
| 4,543,370 A | 9/1985 | Porter et al. |
| 4,643,894 A | 2/1987 | Porter et al. |
| 4,683,256 A | 7/1987 | Porter et al. |
| 4,725,441 A | 2/1988 | Porter et al. |
| 4,802,924 A | 2/1989 | Woznicki et al. |
| 4,873,231 A | 10/1989 | Smith |
| 4,906,478 A | 3/1990 | Valentine et al. |
| 5,234,099 A | 8/1993 | Berta |
| 5,275,822 A | 1/1994 | Valentine et al. |
| 5,424,075 A | 6/1995 | Daher et al. |
| 5,510,385 A | 4/1996 | Stroppolo et al. |
| 5,630,871 A | 5/1997 | Jordan |
| 6,103,260 A | 8/2000 | Luber et al. |
| 6,274,162 B1 | 8/2001 | Steffenino et al. |
| 2004/0146559 A1 * | 7/2004 | Sowden et al. ............... 424/471 |
| 2010/0086591 A1 | 4/2010 | Murachanian et al. |

FOREIGN PATENT DOCUMENTS

| | | | |
|---|---|---|---|
| WO | WO 2005/070417 A1 | 8/2005 | |
| WO | WO2006/047695 A2 * | 5/2006 | ............... A61K 9/20 |
| WO | WO 2006/047695 A2 | 5/2006 | |

OTHER PUBLICATIONS

"The Elizabeth Companies Tablet Design Training Manual" (Elizabeth Carbide Die Co., Inc., p. 7 (McKeesport, Pa), (1989).
Lieberman et al., Pharmaceutical Dosage Forms—Tablets, vol. 2, 2nd Edition. Marcel Dekker Inc., 1990, pp. 213-217, 327-329.
USP 24, 2000 Version. pp. 19-20 and 856 (1999).

(Continued)

*Primary Examiner* — Jane C Oswecki
(74) *Attorney, Agent, or Firm* — Laura A. Donnelly

(57) ABSTRACT

Coated dosage forms comprising a tablet core, preferably in compressed form, that has a coating over its exterior surface and one or more patterns debossed in the tablet surface are disclosed. Methods for manufacturing such dosage forms are also disclosed.

16 Claims, 11 Drawing Sheets

(56) References Cited

OTHER PUBLICATIONS

USP 34-NF29, Section 701, (Nov. 2010).
List PH and Horhammer L (ED): "Hagers Handbuch der pharmazeutischen Praxis passage", Hagers Handbuch Der Pharmazeutischen Praxis, Springer Verlag, Berlin, DE, Jan. 1, 1971, pp. 690-694, XP002396425, the whole document.
International Search Report for PCT/US2013/024384 dated Apr. 22, 2013.

* cited by examiner

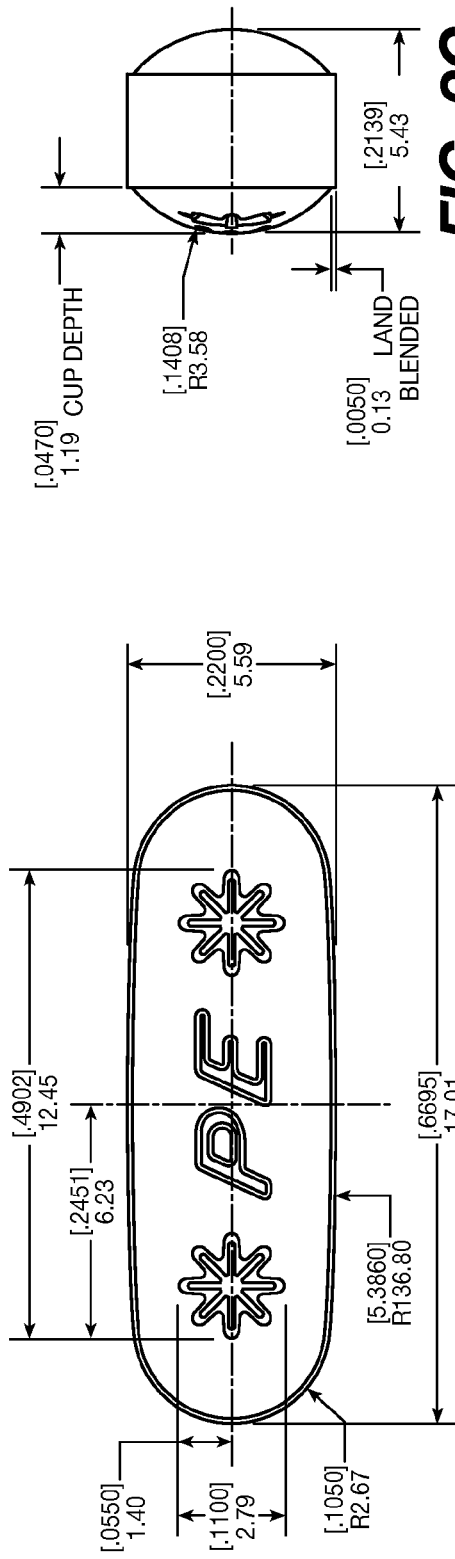
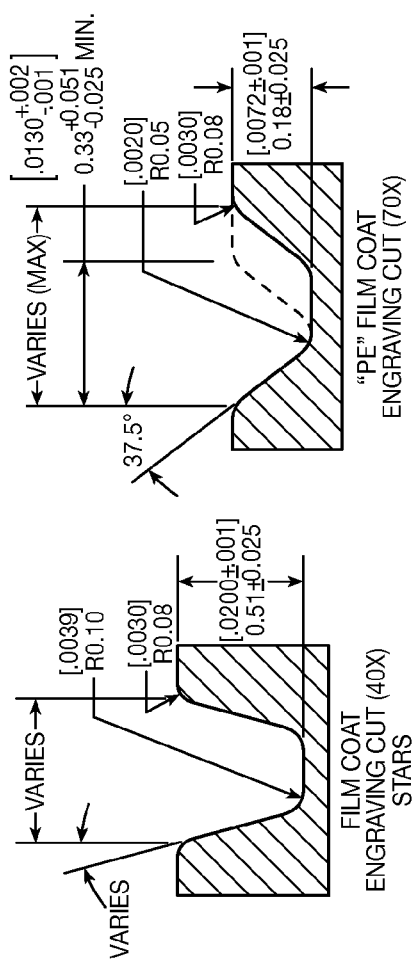
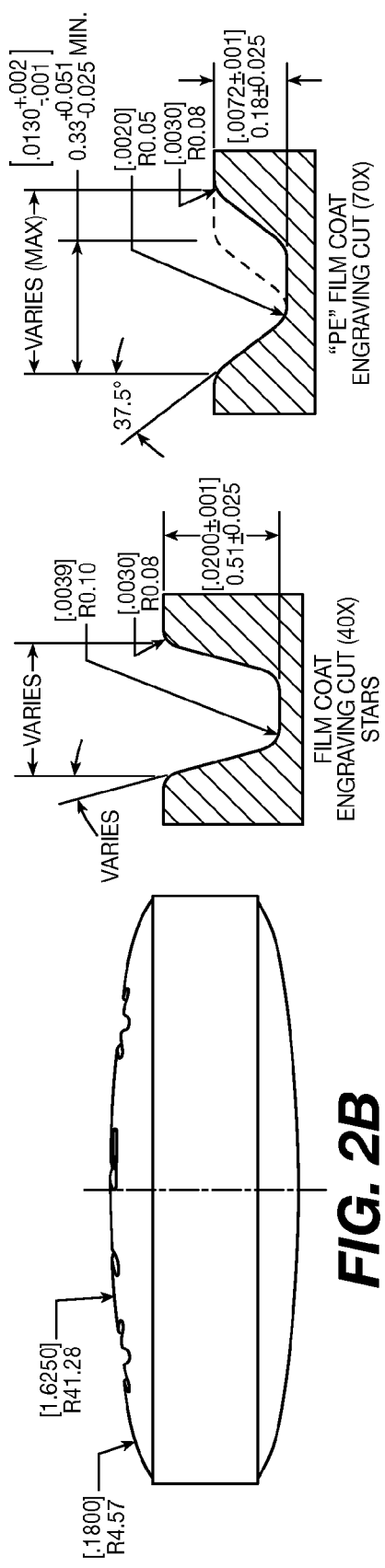

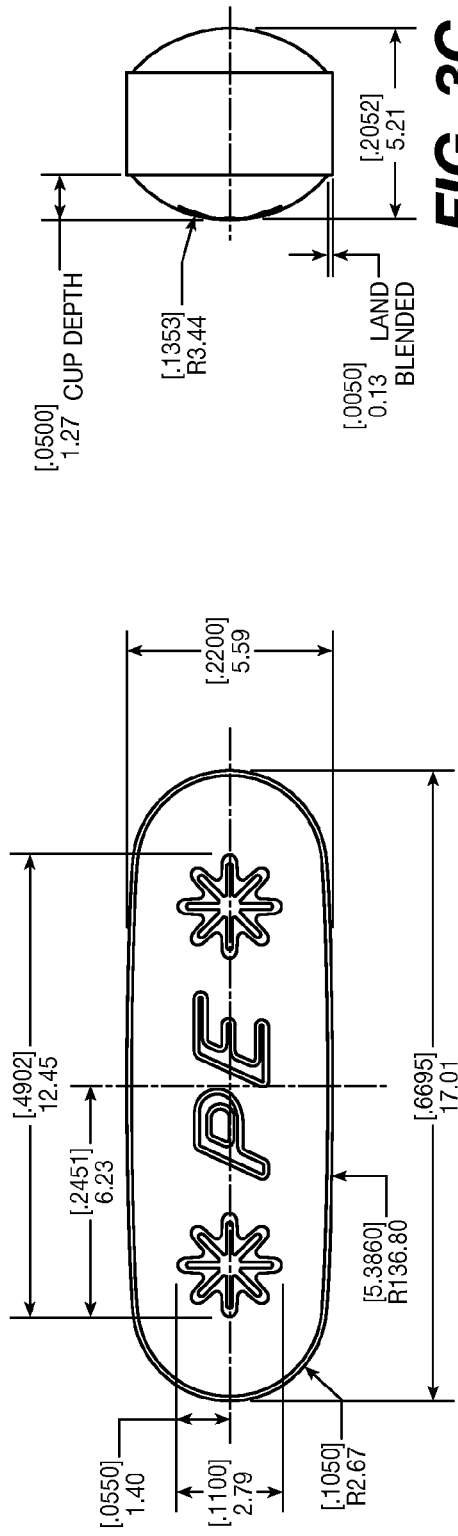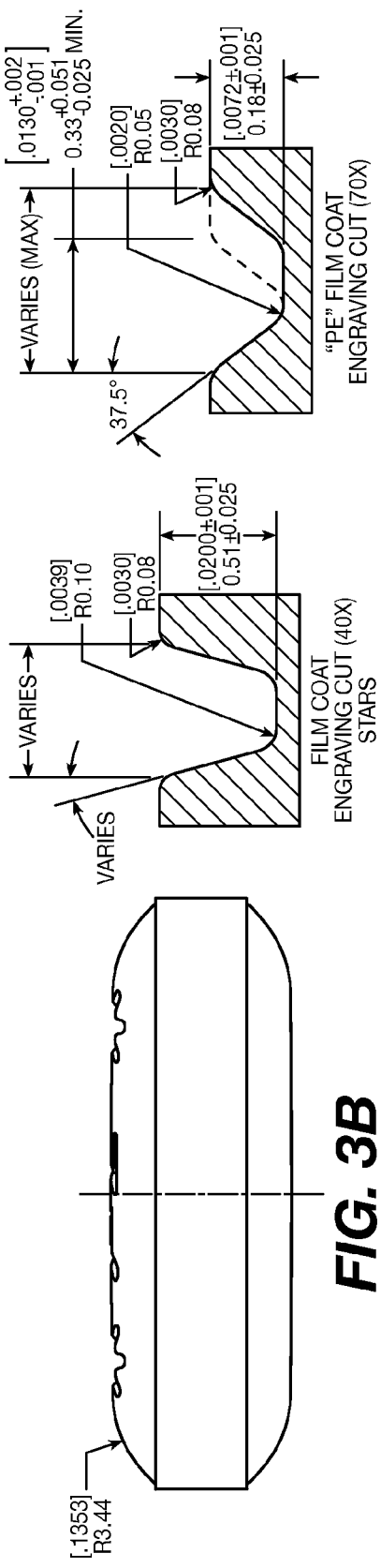

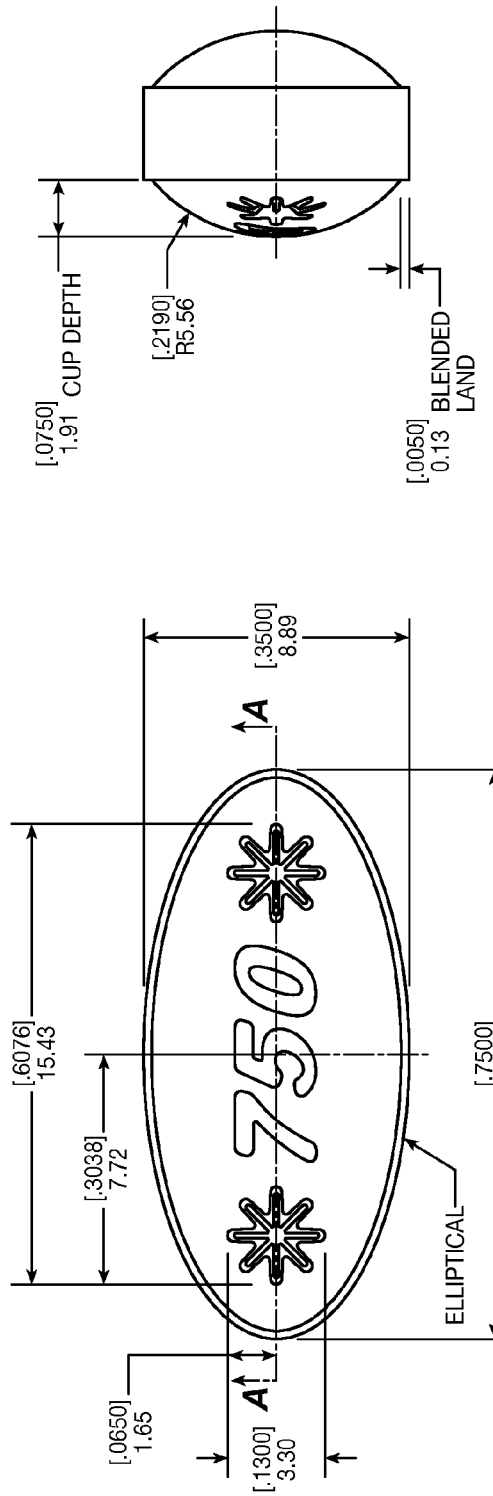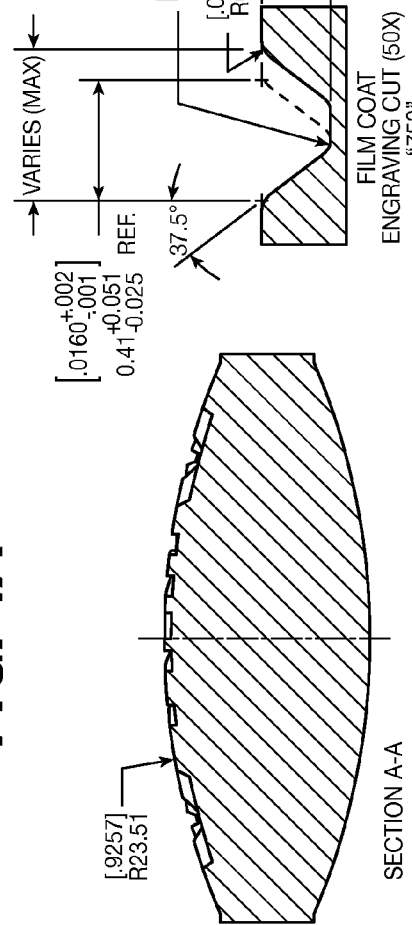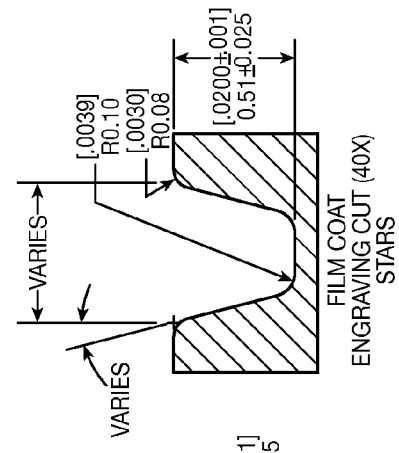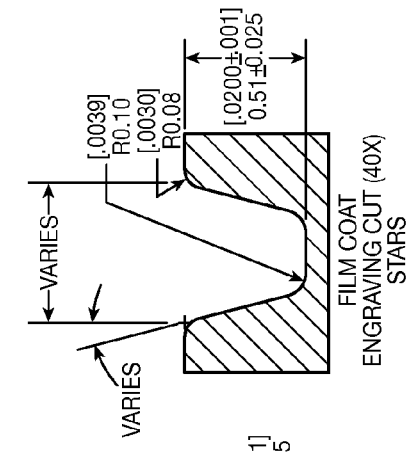
FIG. 4A
FIG. 4B
FIG. 4C
FIG. 4D(i)
FIG. 4D(ii)

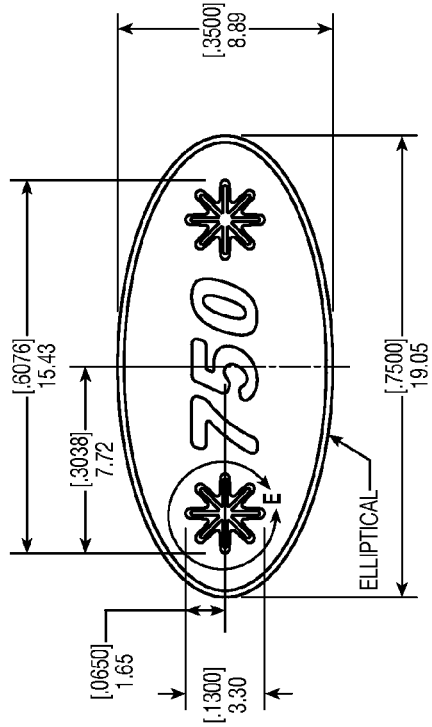
FIG. 5E(i)
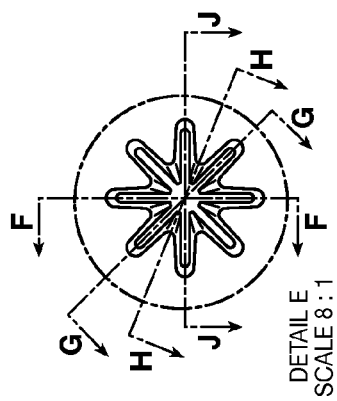
FIG. 5E(ii)
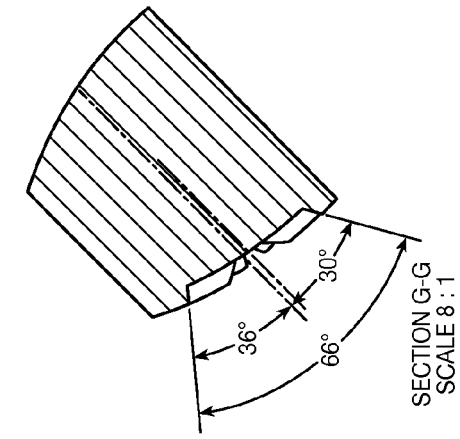
FIG. 5E(vi)
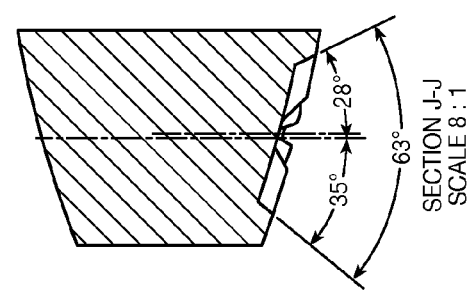
FIG. 5E(v)
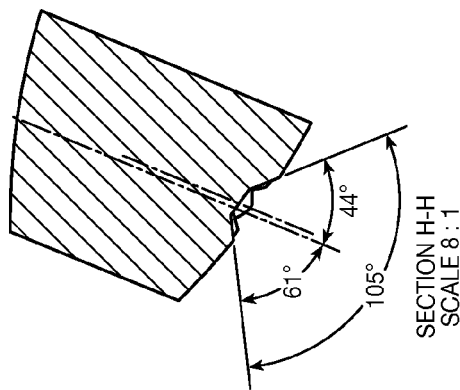
FIG. 5E(iv)
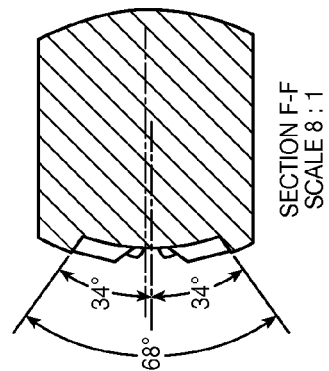
FIG. 5E(iii)

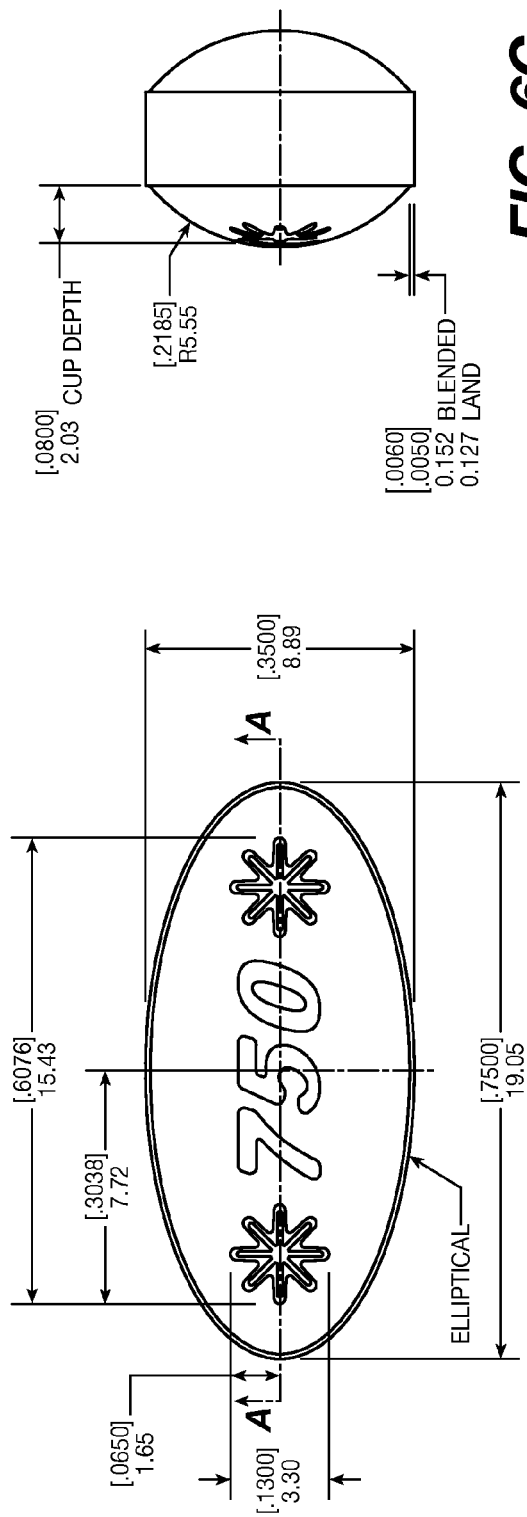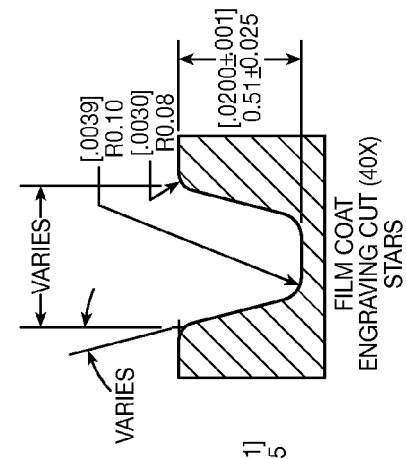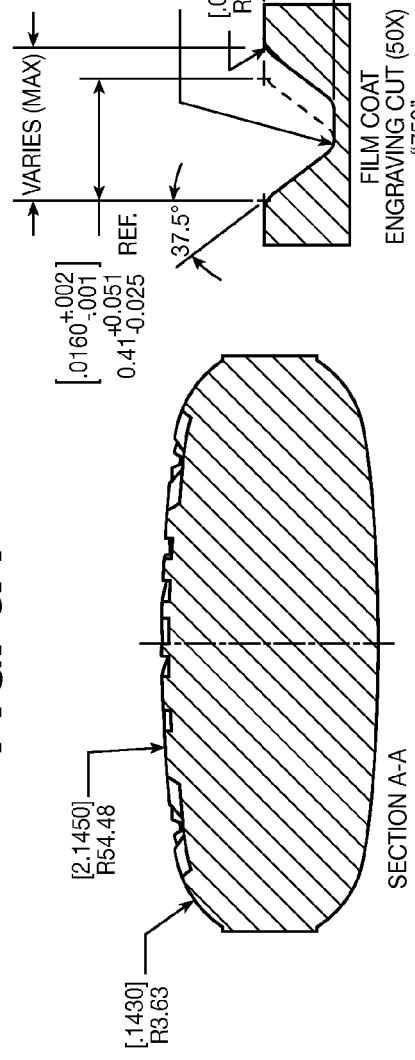

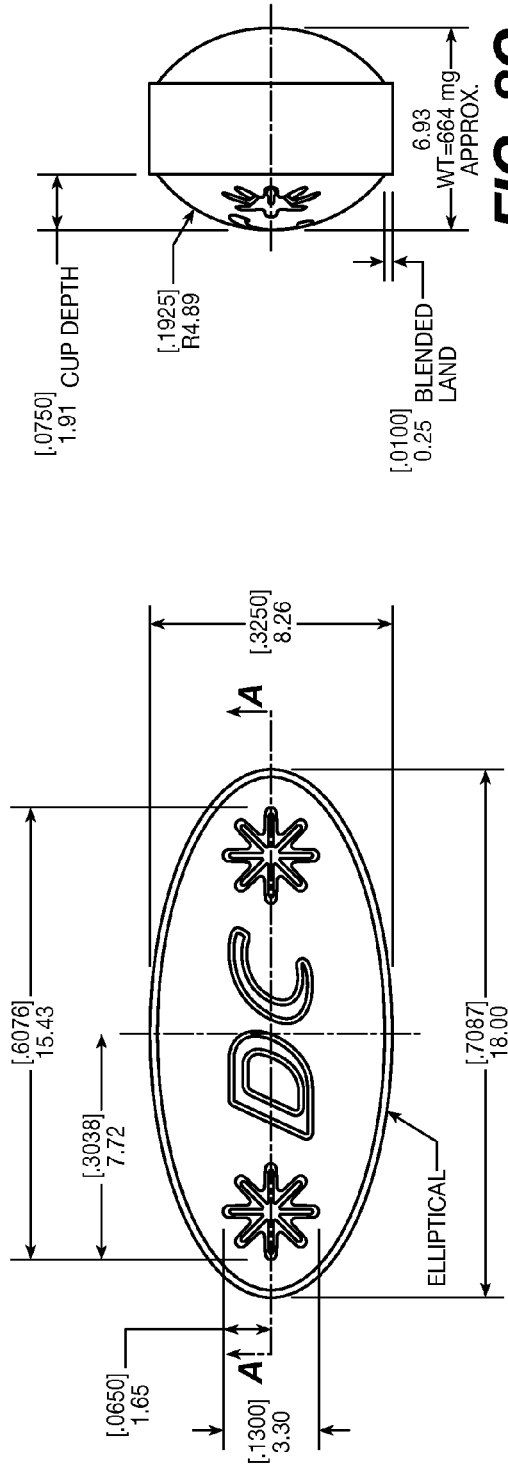
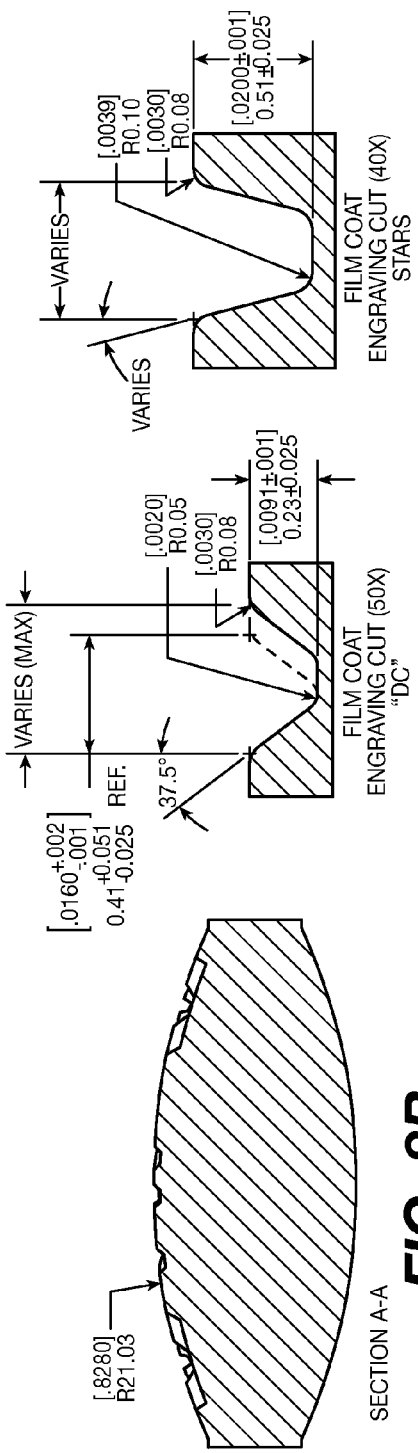

RAPIDLY DISINTEGRATING COATED TABLETS

This application claims priority of the benefits of the filing of U.S. Provisional Application Ser. No. 61/595,767, filed Feb. 7, 2012, the contents of each of which are hereby incorporated by reference in their entirety.

FIELD OF THE INVENTION

The present invention relates to a dosage form comprising a tablet core, preferably in compressed form, that has a coating over its exterior surface and one or more patterns debossed in the tablet surface. The debossed pattern preferably contains at least one that contains a wall angle from vertical of at least about 25 degrees or less. The debossed pattern preferably contains a depth of more than about 0.20 mm.

BACKGROUND OF THE INVENTION

Capsules have long been recognized as a preferred dosage form for the oral delivery of active ingredients, which may be in the form of powder, liquid or granules of different compositions, for delivery to the gastro-intestinal tract of a human. Advantages of capsules as a dosage form include the variety of shapes and color combinations (including different colored caps and bodies), enhancing their unique identification, their glossy elegant appearance, and their easy swallowability. One type of commonly used capsule is a two-piece hard shell capsule, typically made from gelatin, starch, or cellulose derivatives. The hard shell capsule typically comprises a longer body having an outside diameter, and a relatively shorter cap having an inside diameter that will just fit over the outside diameter of the body. The cap fits snugly over the body, creating an overlapping portion of the capsule.

In view of the tamperability of old-fashioned capsules made with hard shell capsule halves of different diameters which can be taken apart, steps have been taken since the 1980s, to manufacture capsule shells which, once assembled, cannot be disassembled without their destruction. One such example is the Capsugel CONI-SNAP® capsule, which has grooves that lock the cap and body together after the capsule has been filled. Another such example is the Parke-Davis KAPSEAL® capsule, in which the body and cap are sealed together using a band of gelatin. Although the sealing or banding of capsule shell halves has, in a large part, proven effective to at least make tampering evident to the consumer, some companies have preferred to manufacture solid dosage forms having densely compacted cores to further reduce the possibility of tampering.

One of the first types of film-coated elongated compressed tablets was referred to as a "caplet". The caplet form offered enhanced swallowability over uncoated tablets due to its elongated shape and film-coated surface, similar to that of the capsule.

There continues to be a need in the pharmaceutical industry to provide over-the-counter coated dosage forms which simulate the appearance of capsules and which identify the source and type of medication provided so that the consumer can readily identify, for example, if the product is a particular type of analgesic or whether it includes antihistamines or other active ingredients in combination with analgesics. Such solid dosage forms have preferably been in the shape of an elongated tablet. The present invention furthers these earlier advances by producing a caplet having faster onset of disintegration and/or dissolution relative to commercially available coated products.

SUMMARY OF THE INVENTION

Tablet compression and coating are two of the most critical aspects of pharmaceutical dosage form manufacturing, since these are the main aspects of the product discernable to the patient consuming the product. Tablet compression tooling is typically designed to produce tablets free of visual defects to the extent permitted by the composition of the tablet and the equipment used in the manufacturing process. Identifying marks and symbols engraved into the tablet surface during compression are generally designed in adherence with established guidelines for shape, size, depth, wall angles, corner rounding, spacing, etc. of the characters to minimize the introduction of defects into debossed designs and to produce legible identification on the tablet following compression and/or coating. In its desired form, batch tablet coating is performed in a manner yielding a homogenous coating appearance free of visual defects and irregularities. When properly applied, conventional tablet coating equipment (coating pans and fluidized bed coaters, etc.) are designed to minimize heterogeneity of the resultant coated tablets, and extensive post-coating processing is required to introduce, or give the appearance of, heterogeneous regions on the tablet surface—including, but not limited to, surface printing, gelatin dipping, overlayer placement, and laser drilling of the coated tablet.

The dosage form may be coated using methods including, but not limited, to spray coating, dip coating, enrobing, and/or electrostatic deposition.

The techniques described herein provide a demonstrated method of preparing solid dosage forms on conventional tablet preparation equipment containing visually identifiable features on the tablet surface that will intentionally produce heterogeneous regions of coating deposition upon conventional tablet coating. In the preferred embodiment, the features intended for heterogeneous coating will contain a measurably decreased coating thickness relative to the surrounding areas of tablet surface, without requiring additional, post-coating processing. In another embodiment, the designed features could contain incompletely (discontinuous) coated regions of tablet surface appearing to visually be fully coated. In one embodiment, the regions of decreased coating will permit the enhanced penetration of water into the tablet core in the specified regions, providing defined, visually identifiable areas for the initiation of tablet disintegration. In one embodiment, the debossed feature provides an enhanced onset of tablet disintegration compared to similar tablets compressed with conventional techniques. One embodiment places the debossed features on curved sections of the tablet surface to minimize compression defects like picking, sticking and bridging of the non-standard compressed shapes.

Another embodiment of the invention would be a tablet produced with a raised feature on the surface (embossed) that would be abraided during the coating process to leave an area on the tablet surface containing less coating than the surrounding area. The less coated area may or may not be visually discernable from the surrounding surface depending on the type and color of coating applied and the relative thicknesses of the coated surface.

BRIEF DESCRIPTION OF THE DRAWINGS

FIG. 2A is an enlarged, schematic top plan view of a standard shaped caplet core having a star pattern debossed in the tablet surface.

FIG. 2B is an enlarged, schematic elevational side view of the caplet core of FIG. 2A.

FIG. 2C is an enlarged, schematic elevational end view of the caplet core of FIG. 2A.

FIG. 2D(i) and FIG. 2D(ii) show the engraving cuts and engineering data for the caplet core of FIG. 2A.

FIG. 3A is an enlarged, schematic top plan view of a standard shaped caplet core having a star pattern debossed in the tablet surface.

FIG. 3B is an enlarged, schematic elevational side view of the caplet core of FIG. 3A.

FIG. 3C is an enlarged, schematic elevational end view of the caplet core of FIG. 3A.

FIG. 3D(i) and FIG. 3D(ii) show the engraving cuts and engineering data for the caplet core of FIG. 3A.

FIG. 4A is an enlarged, schematic top plan view of an ellipse shaped caplet core having a star pattern debossed in the tablet surface.

FIG. 4B is an enlarged, schematic elevational side view of the caplet core of FIG. 4A.

FIG. 4C is an enlarged, schematic elevational end view of the caplet core of FIG. 4A.

FIG. 4D(i) and FIG. 4D(ii) shows the engraving cuts and engineering data for the caplet core of FIG. 4A.

FIGS. 5E(i)-5E(vi) show the details, including the angles, for the engraving cuts for the star shape in the caplet core of FIG. 4A.

FIG. 6A is an enlarged, schematic top plan view of an ellipse shaped caplet core having a star pattern debossed in the tablet surface.

FIG. 6B is an enlarged, schematic elevational side view of the caplet core of FIG. 6A.

FIG. 6C is an enlarged, schematic elevational end view of the caplet core of FIG. 6A.

FIG. 6D(i) and FIG. 6D(ii) shows the engraving cuts and engineering data for the caplet core of FIG. 6A.

FIG. 8A is an enlarged, schematic top plan view of an ellipse shaped caplet core having a star pattern debossed in the tablet surface.

FIG. 8B is an enlarged, schematic elevational side view of the caplet core of FIG. 8A.

FIG. 8C is an enlarged, schematic elevational end view of the caplet core of FIG. 8A.

FIG. 8D(i) and FIG. 8D(ii) shows the engraving cuts and engineering data for the caplet core of FIG. 8A.

DETAILED DESCRIPTION OF INVENTION

As used herein, the term "dosage form" applies to any solid composition designed to contain a specific pre-determined amount (dose) of a certain ingredient, for example an active ingredient as defined below. Suitable dosage forms may be pharmaceutical drug delivery systems, including those for oral administration, buccal administration, rectal administration, topical or mucosal delivery, or subcutaneous implants, or other implanted drug delivery systems; or compositions for delivering minerals, vitamins and other nutraceuticals, oral care agents, flavorants, and the like. In a particularly preferred embodiment, the dosage form is an orally administered system for delivering a pharmaceutical active ingredient to the gastro-intestinal tract of a human. In another preferred embodiment, the dosage form is an orally administered "placebo" system containing pharmaceutically inactive ingredients, and the dosage form is designed to have the same appearance as a particular pharmaceutically active dosage form, such as may be used for control purposes in clinical studies to test, for example, the safety and efficacy of a particular pharmaceutically active ingredient.

As used herein the term "tablet" refers to a solid form prepared by compaction of powders on a tablet press, as well known in the pharmaceutical arts. Tablets can be made in a variety of shapes, including round, or elongated, such as flattened ovoid or cylindrical shapes. As used herein, a "caplet core" refers to one type of elongated, generally cylindrical or capsule-shaped tablet having straight or slightly bowed sides, and a generally circular cross-section, and having a length to diameter ratio from about 2 to about 5, e.g., from about 2.5 to about 3.5, say about 3.

Figure 1:
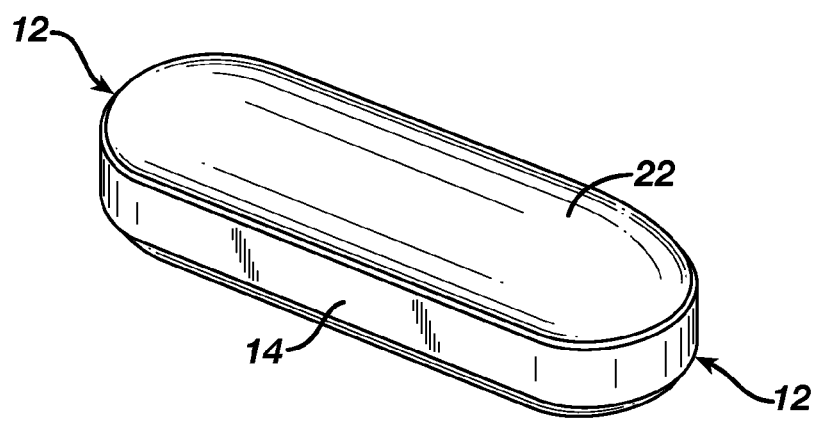
FIG. 1 is an enlarged isometric view of a compressed core in the form of an elongated tablet having a generally cylindrical shape. This form is otherwise known as a caplet.
Figure 5C:
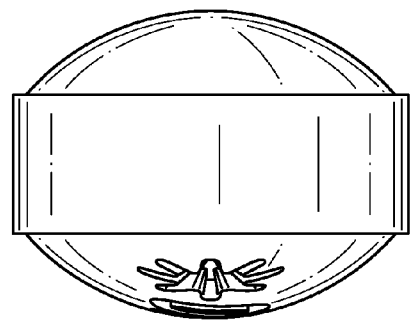
FIGS. 5A-5D are schematics of the top plan view (FIG. 5A), the side view (FIG. 5B), the end view (FIG. 5C) and the back view (FIG. 5D) of the caplet core of FIG. 4A.
Figure 5B:
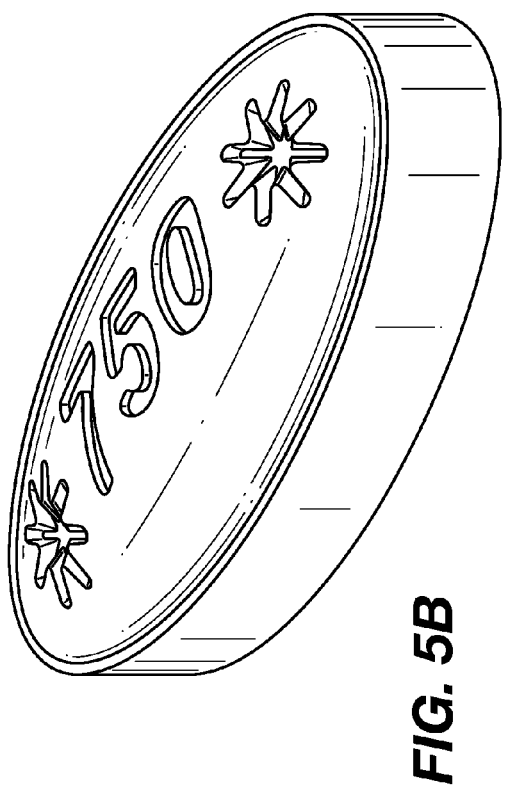
Figure 5A:
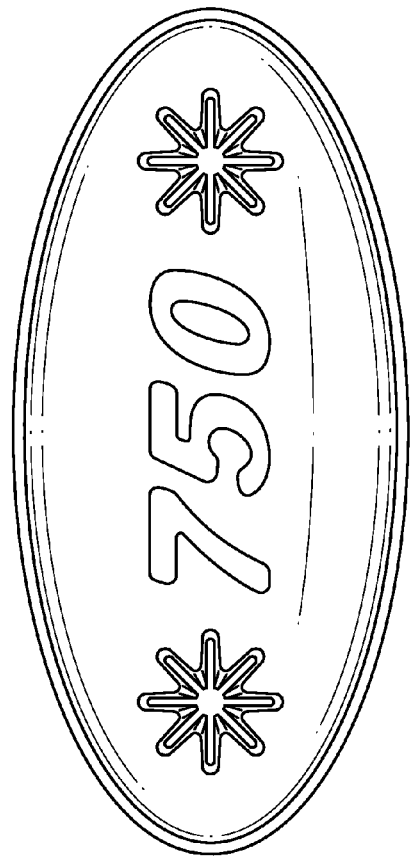
Figure 5D:
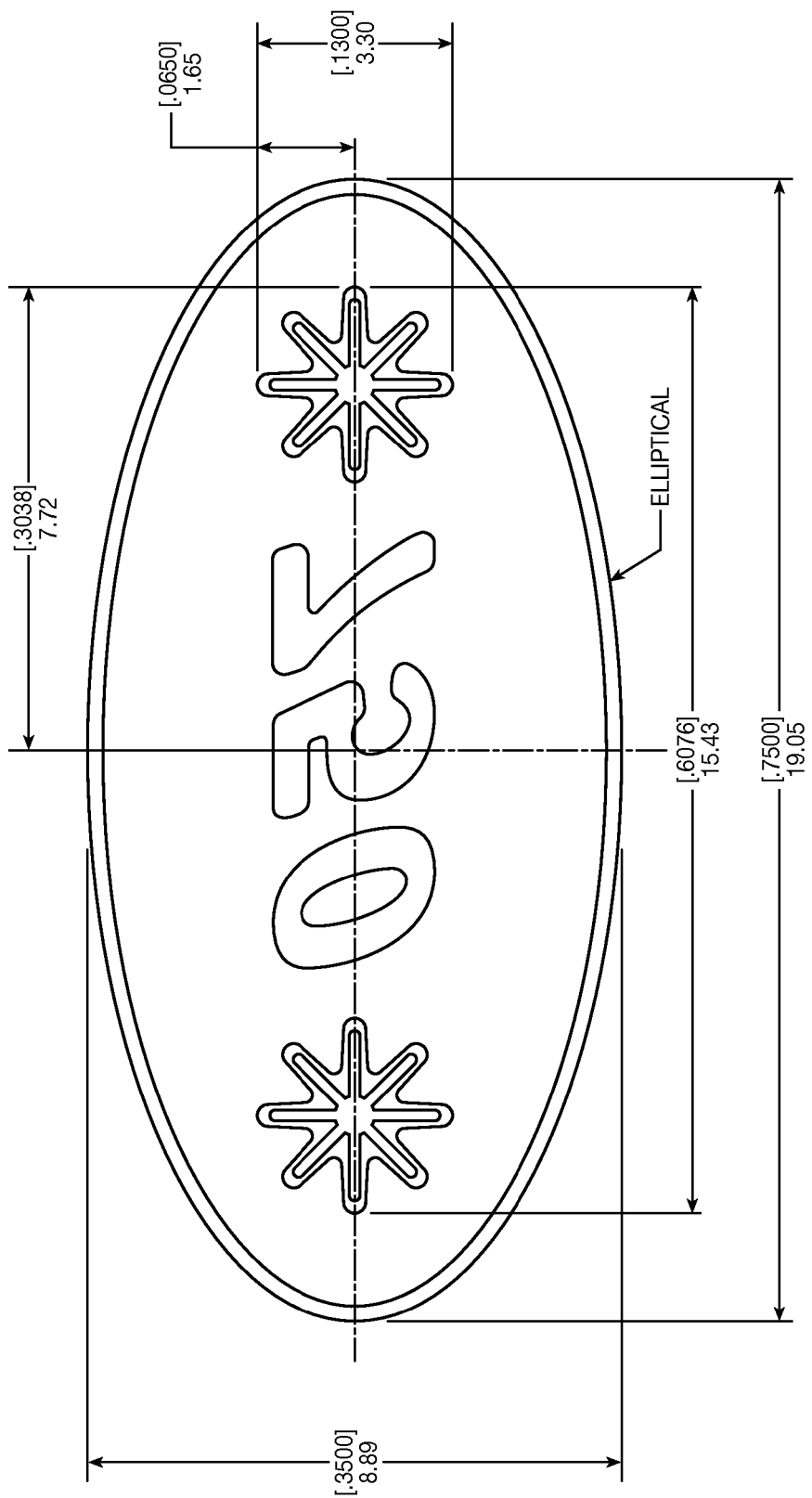
Figure 7C:
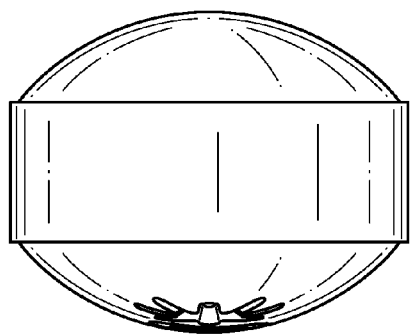
FIGS. 7A-7C are schematics of the top plan view (FIG. 7A), the side view (FIG. 7B) and the end view (FIG. 7C) of the caplet core of FIG. 6A.
Figure 7A:
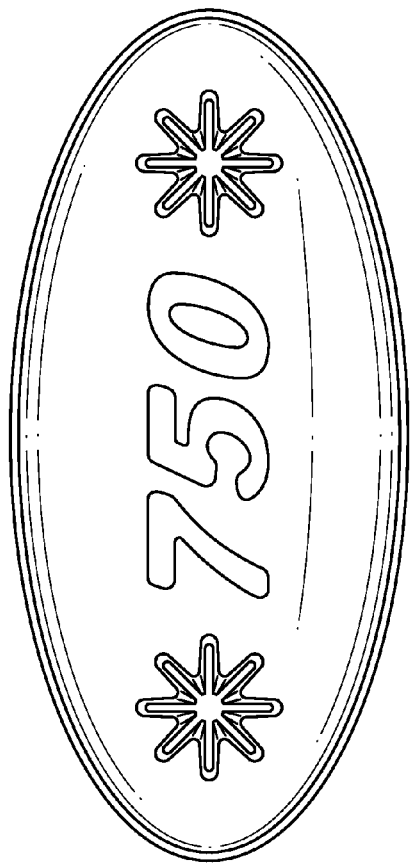
Figure 7B:
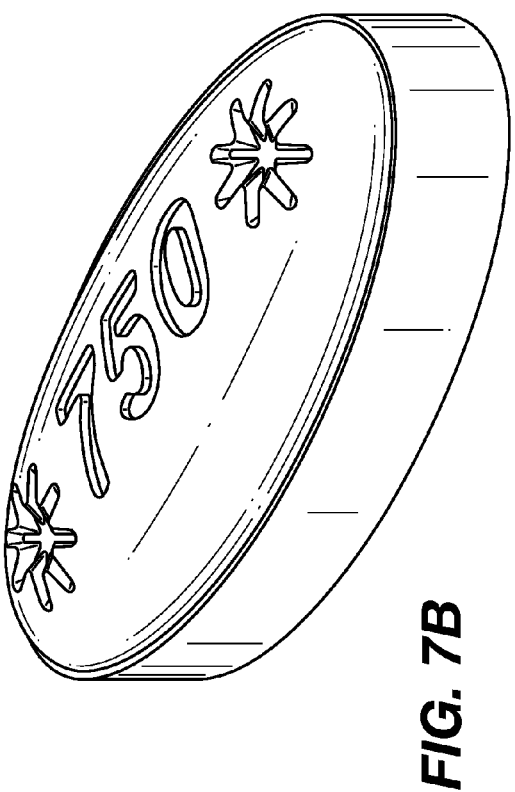
Figure 9C:
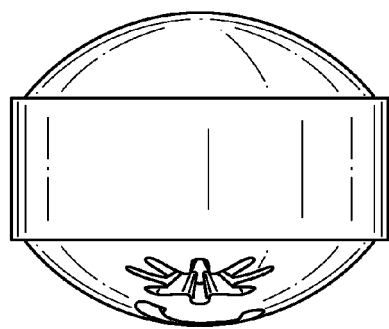
FIGS. 9A-9C are schematics of the top plan view (FIG. 9A), the side view (FIG. 9B) and the end view (FIG. 9C) of the caplet core of FIG. 8A.
Figure 9A:
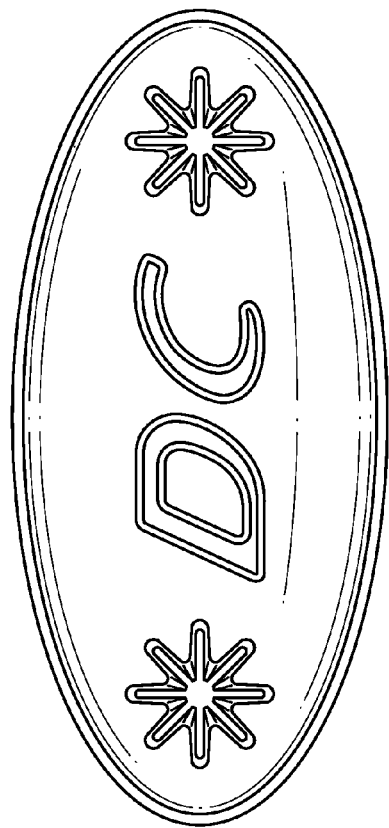
Figure 9B:
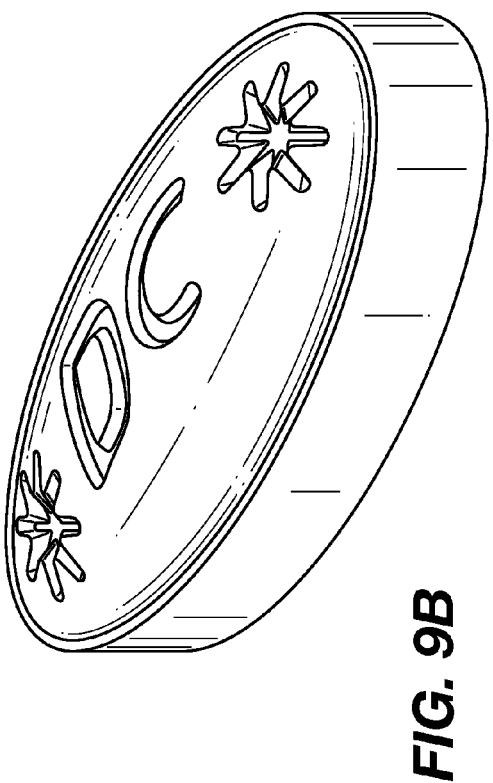

A caplet is one type of elongated tablet covered by a film coating. An example of a standard caplet is shown in FIG. 1. Referring to FIG. 1, a core 10 in the shape of an elongated tablet has two ends 12 at opposing sides of a longitudinal axis. A bellyband 14 occurs along the longitudinal circumference where the tablet is in contact with die walls during compaction. The core 10 can subsequently be covered with a subcoating 22 that can be any number of medicinally acceptable coverings. The use of subcoatings is well known in the art.

The core can have any number of pharmaceutically acceptable tablet shapes. Tablet is meant to encompass shaped compacted dosage forms in the broadest sense. An elongated tablet is a type of tablet having an elongated shape. One type of caplet core shown in FIG. 1 has a generally circular cross section that generally tapers from the mid-section to a tip or end region. For purposes of this application, the longitudinal axis passes through the center of both ends of the caplet core.

The core (or substrate) may be any solid form. The core may prepared by any suitable method, for example the core be a compressed dosage form, or may be molded. As used herein, "substrate" refers to a surface or underlying support, upon which another substance resides or acts, and "core" refers to a material that is at least partially enveloped or surrounded by another material. For the purposes of the present invention, the terms may be used interchangeably: i.e., the term "core" may also be used to refer to a "substrate." Preferably, the core comprises a solid, for example, the core may be a compressed or molded tablet, hard or soft capsule, suppository, or a confectionery form such as a lozenge, nougat, caramel, fondant, or fat based composition.

In one embodiment, the core has one or more major faces. The core may be in a variety of different shapes. For example, in one embodiment the core may be in the shape of a truncated cone. In other embodiments the core may be shaped as a polyhedron, such as a cube, pyramid, prism, or the like; or may have the geometry of a space figure with some non-flat faces, such as a cone, cylinder, or the like. Exemplary core shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling):

Shallow Concave.
Standard Concave.
Deep Concave.
Extra Deep Concave.
Modified Ball Concave.
Standard Concave Bisect.
Standard Concave Double Bisect.
Standard Concave European Bisect.
Standard Concave Partial Bisect.
Double Radius.
Bevel & Concave.
Flat Plain.
Flat-Faced-Beveled Edge (F.F.B.E.).
F.F.B.E. Bisect.
F.F.B.E. Double Bisect.
Ellipse.
Oval.
Capsule.
Rectangle.
Pentagon.
Octagon.
Diamond.
Arrowhead.
Bullet.
Barrel.
Half Moon.
Shield.
Heart.
Almond.
Parallelogram.
Trapezoid.
FIG. 8/Bar Bell.
Bow Tie.
Uneven Triangle.

The core 10 may be pressed of a blend of suitable active ingredients and excipients which may be either their natural color, including white, or can be conventionally colored as desired to provide a conventional, or elongated-shaped core of any desired color.

According to an embodiment, the core may contain a disintegrant and/or a superdisintegrant. Suitable disintegrants for making the core, or a portion thereof, by compression, include, e.g., sodium starch glycolate, cross-linked polyvinylpyrrolidone, cross-linked carboxymethylcellulose, starches, microcrystalline cellulose, and the like. According to an embodiment, the superdisintegrant is present as a percentage of the weight of the core from about 0.05 percent to about 10 percent.

The dosage form of the present invention preferably contains one or more active ingredients. Suitable active ingredients broadly include, for example, pharmaceuticals, minerals, vitamins and other nutraceuticals, oral care agents, flavorants and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, oral contraceptives, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotidine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

In one embodiment of the invention, at least one active ingredient may be selected from bisacodyl, famotidine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, at least one active ingredient is selected from analgesics, anti-inflammatories, and antipyretics, e.g., non-steroidal anti-inflammatory drugs (NSAIDs), including a) propionic acid derivatives, e.g., ibuprofen, naproxen, ketoprofen and the like; b) acetic acid derivatives, e.g., indomethacin, diclofenac, sulindac, tolmetin, and the like; c) fenamic acid derivatives, e.g., mefenamic acid, meclofenamic acid, flufenamic acid, and the like; d) biphenylcarbodylic acid derivatives, e.g., diflunisal, flufenisal, and the like; e) oxicams, e.g., piroxicam, sudoxicam, isoxicam, meloxicam, and the like; f) cyclooxygenase-2 (COX-2) selective NSAIDs; and g) pharmaceutically acceptable salts of the foregoing.

In one particular embodiment, at least one active ingredient is selected from propionic acid derivative NSAID, which are pharmaceutically acceptable analgesics/non-steroidal anti-inflammatory drugs having a free —CH(CH$_3$)COOH or —CH$_2$CH$_2$COOH or a pharmaceutically acceptable salt group, such as —CH(CH$_3$)COO—Na+ or CH$_2$CH$_2$COO—Na+, which are typically attached directly or via a carbonyl functionality to a ring system, preferably an aromatic ring system.

Examples of useful propionic acid derivatives include ibuprofen, naproxen, benoxaprofen, naproxen sodium, fenbufen, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen, bucloxic acid, and pharmaceutically acceptable salts, derivatives, and combinations thereof In one embodiment of the invention, the propionic acid derivative is selected from ibuprofen, ketoprofen, flubiprofen, and pharmaceutically acceptable salts and combinations thereof In another embodiment, the propionic acid derivative is ibuprofen, 2-(4-isobutylphenyl)propionic acid, or a pharmaceutically acceptable salt thereof, such as the arginine, lysine, or histidine salt of ibuprofen. Other pharmaceutically acceptable salts of ibuprofen are described in U.S. Pat. Nos. 4,279,926, 4,873,231, 5,424,075 and 5,510,385, the contents of which are incorporated by reference.

In another particular embodiment of the invention, at least one active ingredient may be an analgesic selected from acetaminophen, acetyl salicylic acid, ibuprofen, naproxen, ketoprofen, flurbiprofen, diclofenac, cyclobenzaprine, meloxicam, rofecoxib, celecoxib, metamizol sodic (dypirone), caffeine, and pharmaceutically acceptable salts, esters, isomers, and mixtures thereof.

In another particular embodiment of the invention, at least one active ingredient may be selected from pseudoephedrine, phenylpropanolamine, chlorpheniramine, carbinoxamine, doxylamine, dextromethorphan, diphenhydramine, astemizole, terfenadine, fexofenadine, loratadine, desloratadine, cetirizine, acetylcysteine, guaifenesin, carbocysteine, ambroxol, bromhexine, mixtures thereof and pharmaceutically acceptable salts, esters, isomers, and mixtures thereof.

In another particular embodiment, at least one active ingredient is an NSAID and/or acetaminophen, and pharmaceutically acceptable salts thereof.

The active ingredient or ingredients are present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dosing regimen, the age and weight of the patient, and other factors should be considered, as known in the art. Typically, the dosage form comprises at least about 1 weight percent, preferably, the dosage form comprises at least about 5 weight percent, e.g., about 20 weight percent of one or more active ingredients. In one preferred embodiment, the core comprises a total of at least about 25 weight percent (based on the weight of the core) of one or more active ingredients.

The active ingredient or ingredients may be present in the dosage form in any form. For example, one or more active ingredients may be dispersed at the molecular level, e.g., melted or dissolved, within the dosage form, or may be in the form of particles, which in turn may be coated or uncoated. If an active ingredient is in form of particles, the particles (whether coated or uncoated) typically have an average particle size of about 1-2000 microns. In one preferred embodiment, such particles are crystals having an average particle size of about 1-300 microns. In another preferred embodiment, the particles are granules or pellets having an average particle size of about 50-2000 microns, preferably about 50-1000 microns, most preferably about 100-800 microns.

In a preferred embodiment, the dissolution characteristics of the at least one active ingredient follow an "immediate release profile". As used herein, an immediate release profile is one in which the active ingredient dissolves without substantial delay or retardation due to the dosage form. This can be contrasted with the dissolution of modified release, e.g., delayed or controlled release dosage forms known in the art. In one embodiment, the dissolution rate of the immediately released active ingredient from the dosage form of the invention is within about 20% of the dissolution rate of the active ingredient from a pure crystalline powder of said active ingredient, e.g., the time for 50%, 75%, 80%, or 90% dissolution of active ingredient from the dosage form is not more than 20% longer than the corresponding time for 50%, 75%, 80%, or 90% dissolution of active ingredient from a pure crystalline powder of said active ingredient. In another embodiment, the dissolution of the immediately released active ingredient from the dosage form of the invention meets USP specifications for immediate release tablets, gelcaps, or capsules containing the active ingredient. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing; and for acetaminophen and codeine phosphate capsules USP 24 specifies that at least 75% of the acetaminophen contained in the dosage form is dissolved within 30 minutes in 900 mL of 0.1 N Hydrochloric acid using USP Apparatus 2 (paddles) at 50 rpm; and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes. See USP 24, 2000 Version, 19-20 and 856 (1999). In yet another embodiment, wherein the immediately released active ingredient is acetaminophen, when tested in 37° C. water using USP Apparatus II (paddles) at 50 rpm, at least 80%, preferably at least 85%, of the acetaminophen contained in the dosage form is released therefrom within 30 minutes.

In yet another embodiment, the time for release of at least 80%, preferably at least 85%, of at least one active ingredient contained in the dosage form is released therefrom is not more than about 50%, e.g., not more than about 40% of the time specified by the dissolution method for immediate release listed in the United States New Drug Application for that particular active ingredient.

In one particularly preferred embodiment, wherein the immediately released active ingredient is acetaminophen, when tested in 37° C. water using USP Apparatus II (paddles) at 50 rpm, at least 80% of the acetaminophen contained in the dosage form is released therefrom within about 6 minutes, e.g., within about 5 minutes, or within about 3 minutes.

In one embodiment the tablet, coating, and coating at the debossed positions can be observed using the USP Disintegration test as outlined in USP 34-NF29, Section 701. In another embodiment the tablet, coating and coating at the debossed positions can be observed by placing the tablet into water at 37° C. without agitation.

According to an embodiment, disintegration without agitation can be observed at the spoke portions of the tablet at less than about 30 seconds, e.g., less than about 15 seconds, e.g., less than about 10 seconds, e.g., less than about 5 seconds.

In certain preferred embodiments, the core is covered with a coating that can be any number of medicinally acceptable coverings. The use of coatings is well known in the art and disclosed in, for example, U.S. Pat. No. 5,234,099, which is incorporated by reference herein. Any composition suitable for film-coating a tablet may be used as a coating according to the present invention. Examples of suitable coatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable compositions for use as coatings include those manufactured by Colorcon, a division of Berwind Pharmaceutical Services, Inc., 415 Moyer Blvd., West Point, Pa. 19486 under the tradename "OPADRY®" (a dry concentrate comprising film forming polymer and optionally plasticizer, colorant, and other useful excipients). Additional suitable coatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as Polysorbate-80, sodium lauryl sulfate and dioctyl-sodium sulfosuccinate; polycarbohydrates, pigments, opacifiers.

Preferred coatings include water soluble polymers selected from the group consisting of hydroxypropylmethyl cellulose, hydroxypropyl cellulose, methyl cellulose, polymethacrylates, polyvinyl alcohol, polyvinyl alcohol:polyethylene glycol copolymers and mixtures thereof According to an embodiment, the average thickness of the coating, excluding debossed pattern areas of the core, is preferably in the range from about 1 to about 150 microns, or from about 50 to about 90 microns, or from about 10 to about 90 microns, or from about 20 to about 80 microns, or from about 30 to about 70 microns. In certain embodiments, the thickness of the coating at the location of the debossed pattern typically ranges from about 0 to about 100 microns, or from about 20 to about 80 microns, or from about 30 to about 70 microns. The thickness of the coating, which will vary depending on the % weight gain that the coating contributes to the dosage form, will be less at the location of the debossed pattern as compared to the thickness of the coating at areas excluding the debossed pattern. Preferably, the thickness of the coating at the location of the debossed pattern is about 25 to about 55%, or about 30 to about 50% less than the thickness of the coating at areas excluding the debossed pattern.

In one embodiment, the coating comprises from about 10 percent to about 50 percent, e.g., from about 15 percent to about 20 percent of HPMC. The dried coating typically is present in an amount, based upon the dry weight of the core, from above about 0 percent to about 5 percent, or from about 1 percent to about 4 percent, or from about 2 percent to about 3 percent, or from about 1 to about 2 percent. The coat is typically provided by spraying in a coating pan or fluidized bed to cover the tablet in a conventional manner. The coating composition is optionally tinted or colored with colorants such as pigments, dyes and mixtures thereof.

In one embodiment, coating is initially applied to the entire exterior surface of core. Coating can be applied as a clear, transparent coating such that the core can be seen. The choice is dictated by the preference of the manufacturer and the economics of the product. In a preferred embodiment, a commercially available pigment is included the coating composition in sufficient amounts to provide an opaque film having a visibly distinguishable color relative to the core.

In a preferred embodiment of the invention, the dosage form comprises one or more debossed patterns. Preferably, the debossed pattern contains at least one wall and the at least one wall contains a wall angle from vertical of about 25 degrees or less, more preferably of about 20 degrees or less, or about 15 degrees or less. Preferably, the debossed pattern contains a depth of more than about 0.20 mm, or more than about 0.50 mm, or up to about 0.70 mm.

Preferably, the debossed pattern comprises three or more extensions or "spokes" extending radially from a central hub. In one embodiment, the one or more debossed patterns comprise one or more eight-spoke debossed patterns. In another embodiment, two debossed patterns appear on opposite sides of a single face of the dosage form.

In one embodiment the dosage form of the present invention is a multilayer tablet, e.g., a trilayer tablet or a bilayer tablet. In this embodiment two debossed patterns are on a single face of the bilayer tablet. In a further embodiment the bilayer tablet comprises a modified or sustained release layer and an immediate release layer, wherein the debossed portions are on the face of the immediate release layer.

In one embodiment the debossed patterns have a deep well in the spokes of said patterns, which acts to disrupt the coating integrity during a film coating process. This results in a dosage form wherein the coating disintegrates at a faster rate than the coating at other portions of the tablet.

In one embodiment the coating level and thickness within the well of the spokes is lower than at the surface face of the tablet, e.g., at least about 10% lower, at least about 20% lower, at least about 30% lower, at least about 40% lower, at least about 50% lower, or at least about 60% lower.

One preferred process of manufacturing intermediate dosage form 20 begins by compressing or compacting a tablet core 10 into the desired shape of the medicament. As used herein, "compact, compacting, or compacted" and "compress, compressing, or compressed" may be used interchangeably to describe the commonly used process of compacting powders into tablets via conventional pharmaceutical table ting technology as well known in the art. One typical such process employs a rotary tablet machine, often referred to as a "press" or "compression machine", to compact the powders into tablets between upper and lower punches in a shaped die. This process produces a core having two opposed faces, formed by contact with an upper and lower punch, and having a bellyband formed by contact with a die wall. Typically such compressed tablets will have at least one dimension of the major faces at least as long as the height of the bellyband area between the major faces. Alternately, processes have been disclosed in the prior art to enable the "longitudinal compression" of tablet cores. When longitudinally compressed tablets are employed, it has been found that an aspect ratio (height between the major faces to width or diameter of the major faces) from about 1.5 to about 3.5, e.g., about 1.9 facilitates handling.

Tablets are typically compacted to a target weight and "hardness". Hardness is a term used in the art to describe the diametrical breaking strength as measured by conventional pharmaceutical hardness testing equipment, such as a Schleuniger Hardness Tester. In order to compare values across differently sized tablets, the breaking strength is normalized for the area of the break (which may be approximated as tablet diameter times thickness). This normalized value, expressed in kp/cm2, is sometimes referred in the art as "tablet tensile strength." A general discussion of tablet hardness testing is found in Leiberman et al., Pharmaceutical Dosage Forms—Tablets, Volume 2, 2nd ed., Marcel Dekker Inc., 1990, pp. 213-217, 327-329, which is incorporated by reference herein.

The medicaments manufactured according to the present invention, therefore, provide the desired shape, swallowability and appearance for a solid dosage form. Further, the dosage form of the invention provides improved onset of dissolution and disintegration, while not compromising swallowability of the dosage form.

It will become apparent to those skilled in the art that various modifications to the preferred embodiments of the invention can be made by those skilled in the art without departing from the spirit or scope of the invention as defined by the appended claims.

EXAMPLES

Example 1

Preparation of Acetaminophen Ellipse-Shaped Caplets

Part A: Compressed Debossed Ellipse-Shaped Caplets with Star Pattern: Compap-L Coarse Acetaminophen granulation, commercially available from the Mallinckrodt Corporation was compressed into ellipse shaped caplets using 0.7500×0.3500 inch tooling on a rotary tablet press. The ellipse shaped caplets, which were compressed with varying cup shapes and depths of 1.91 mm to 2.54 mm, each contained two, 3.3 mm diameter debossed star patterns having a depth of about 0.51 mm and wall angles from vertical of about 25 degrees or less. The caplets were compressed at 833.33 mg.

Part B: Compressed Debossed Ellipse-Shaped Caplets without Star Pattern: Another portion of the Compap-L Coarse Acetaminophen granulation blend can be used to compress caplets in accordance with A above, but without including the debossed the star patterns.

Example 2

Preparation of Film Coating Solution Containing Polyvinyl Alcohol (PVA)

834 g of sterile water for irrigation was added to a stainless steel vessel. A Lightning laboratory mixer was set to about 200-400 RPM and 150.0 grams of PVA based film coating polymer containing red colorant, which is commercially available from the Colorcon corporation as Opadry II®, was added. The film coating solution was mixed for at least 30 minutes.

Example 3

Film Coating of Cores using Polyvinyl Alcohol (PVA) Coating

Immediate release tablet cores containing Acetaminophen were compressed using elliptical shaped tablet tooling containing two, eight pointed stars. A 15" diameter side ventilated coating pan was loaded with 200 grams of 0.6693"×0.3150" tablet cores containing two, 3.0 mm diameter stars and 1800 grams of 0.7500×0.3250" tablet cores containing two, 3.3 mm diameter stars. 400 grams of the coating solution prepared in Example 2 was applied to the preheated tablet cores as an aqueous spray over approximately 22 minutes to a target weight gain of 3.0%.

Example 4

Disintegration of Coated Caplets with and without Debossing

Coated caplets with various debossing patterns can be evaluated for disintegration, utilizing 200 mL of purified water at 37° C. without agitation. The disintegration time at the points of debossing can be examined, as well as disintegration of the coat at other portions of the dosage form. The caplets can be added to the water and visually examined for disintegration at various time points. Table 1 shows the comparisons that can be made in accordance with this example.

TABLE 1

| Sample | Coating and Level Type | Disintegration Time at Star Pattern Debossing (s) | Disintegration Time at remaining coating portions (s)* |
|---|---|---|---|
| Coated Caplet (Standard Shape): | HPMC, 3.5% | Would need to be visually observed. | Would need to be visually observed. |

TABLE 1-continued

| Sample | Coating and Level Type | Disintegration Time at Star Pattern Debossing (s) | Disintegration Time at remaining coating portions (s)* |
|---|---|---|---|
| Debossed Star Shape Pattern Coated Caplet (Standard Shape): no Star debossing | HPMC, 3.5% | Would need to be visually observed. | Would need to be visually observed. |
| Coated Caplet (Ellipse Shape): Debossed Star Shape | HPMC, 3.5% | Would need to be visually observed. | Would need to be visually observed. |
| Coated Caplet (Ellipse Shape): no Star debossing | HPMC, 3.5% | Would need to be visually observed. | Would need to be visually observed. |

*Defined as the time at which another part (i.e., other than the star pattern) of the coating disintegrates.

Example 5

Varying Tooling and Effects on Debossed Bridging

Various dosage forms containing single active and multiple active were observed to determine the effects of cup depth and cup radius on sticking and bridging between the debossed star patterns. Results appear in Table 2 below. At a cup radius above 50, and a ratio of the radius/length above 2.43, bridging and sticking to punch tip surfaces between the branches on the star patterns was observed.

TABLE 2

Evaluation of Compression on Various Tablet Shapes with Star Embossing

| Tablet Type | Tablet Length* | Cup Depth* | Cup Radius* | Ratio of Radius/Depth | Ratio of Radius/Length | % of Tablets Sticking* |
|---|---|---|---|---|---|---|
| Ellipse Shaped Caplet | 19.05 | 2.03 | 54.48 | 26.84 | 2.86 | 75%+ |
| Ellipse Shaped Caplet | 19.05 | 1.91 | 23.51 | 12.31 | 1.23 | <5% |
| Standard Caplet | 17.01 | 1.27 | 100.0 | 78.74 | 5.88 | 35%+ |
| Standard Caplet | 17.01 | 1.19 | 41.28 | 34.69 | 2.43 | <5% |

*Measurements are in mm.
**Sticking is the description of bridging between arms of the debossed star patterns.

Example 6

Preparation of Bilayer Tablet

Acetaminophen controlled release granulation which is commercially available in Tylenol® 8 Hour tablets can be compressed into a bilayer ellipse tablet with Compap-L immediate release granulation on a rotary tablet press. The immediate release side of the tablets can be debossed with the star pattern as described in Example 1.

Example 7

Acetaminophen and Caffeine Cores

Core tablet blends were prepared utilizing the formula shown in Table 3. Acetaminophen, commercially available from Mallinckrodt Corporation, was blended with caffeine, powdered cellulose, sodium starch glycolate, and pregelatinized starch in a fluid bed granulator. A solution of corn starch in water was prepared and sprayed onto the mixture and dried to form a granulation. The granulation was mixed with magnesium stearate and compressed using 18.00 mm×8.26 mm elliptical shaped tooling containing two, 3.3 mm diameter stars.

TABLE 3

Formulation for Acetaminophen and Caffeine Tablets.

|  | Unit Weight (mg) | Weight Percent (per tablet) |
|---|---|---|
| Granulation |  |  |
| Acetaminophen USP | 500.00 | 75.0 |
| Caffeine (commercially available from the BASF corporation) | 65.00 | 10.0 |
| Powdered Cellulose NF (Solka Floc) | 33.253 | 5.00 |
| Sodium Starch Glycolate NF | 16.523 | 3.00 |
| Pregelatinized Starch | 10.004 | 1.00 |
| Magnesium Stearate | 3.220 | 0.50 |
| Granulating Solution |  |  |
| Corn Starch NF | 40.00 | 6.00 |
| Purified Water USP (removed on drying) | — | — |
| Total Compressed Tablet Weight | 668.0 |  |

Example 8

Coated Core with Red HPMC Coating Solution

An HPMC Coating solution was prepared utilizing Opadry Clear, FD&C Red, F&D Yellow and Titanium Dioxide. This solution was applied to the cores in Example 7 at a coating level of 2.56% per coated tablet.

Example 9

Thickness of Coating Levels (Analysis 1)

Coated caplets were evaluated for coating thickness. Measurements at the surface of the caplet and within the depth of the debossed star pattern were taken and compared. Measurements of coating thickness were performed utilizing an Environmental Scanning Electron Microscope (ESEM). A single lot of core tablets was coated with 3 coating trials utilizing the HPMC coating from Example 8 and analyzed. Results are in Table 4. The results demonstrate an average of at least about 30% greater coating thickness at the outside surface over the coating thickness on the inside star arm, with an average of 35.97%.

TABLE 4

Coating Thickness Measurement

| Sample | Coat Thickness Tablet Surface (μm) | Avg Coat Thickness Tablet Surface (μm) | Coat Thickness in Star Arm (μm) | Avg Coating Thickness in Star Arm (μm) | % Difference |
|---|---|---|---|---|---|
| Coated Caplet Trial 1 | 87.78 | 87.78 | 51.95 42.82 45.03 | 46.60 | 46.91 |
| Coated Caplet Trial 2 | 49.83 87.28 | 68.56 | 43.23 45.25 41.70 | 43.39 | 36.70 |
| Coated Caplet Trial 3 | 51.55 52.66 | 52.11 | 33.63 43.06 32.62 | 36.44 | 30.07 |
| Average | 65.82 |  | 42.14 |  | 35.97 |

*Avg = Average

The foregoing examples are not intended to limit the scope of the present invention, which may be set out in the claims. In particular, various equivalents and substitutions will be recognized by those skilled in the art in view of the foregoing disclosure and these are contemplated to be within the scope of the invention.

Example 10

Visual Observation of Disintegration of Coated Tablet with Debossing

A coated caplet prepared in accordance with Examples 2 and 3 was evaluated for disintegration, utilizing 200 mL of purified water at 25° C. without agitation. The caplet was added to the water and visually examined for disintegration at various time points. Disintegration of the coating at the points of debossing as well at other portions of the dosage form was examined Table 5 presents the results.

TABLE 5

| Time | Visual Observation of Disintegration at Star Pattern Debossing(s) | Visual Observation of Disintegration at remaining coating portions(s)* |
|---|---|---|
| 1 sec | None observed | None observed |
| 2 sec | None observed | None observed |
| 3 sec | None observed | None observed |
| 4 sec | Some observed | None observed |
| 5 sec | Some observed; amount released progressively increasing | None observed |
| 6 sec | Some observed; amount released progressively increasing | None observed |
| 7 sec | Some observed; amount released progressively increasing | None observed |
| 8 sec | Some observed; amount released progressively increasing | None observed |
| 9 sec | Some observed; amount released progressively increasing | Very little observed in other area ("500" number in center) |
| 10 sec | Some observed; amount released progressively increasing | Very little observed in other area ("500" number in center) |
| 12 sec | Some observed; amount released progressively increasing | Some observed in other area ("500" number in center); amount released progressively increasing |
| 15 sec | Some observed; amount released progressively increasing | Some observed in other area ("500" number in center); amount released progressively increasing |
| 20 sec | Some observed; amount released progressively increasing | Some observed in other area ("500" number in center); amount released progressively increasing |
| 25 sec | Some observed; amount released progressively increasing | Some observed in other area ("500" number in center); amount released progressively increasing |

TABLE 5-continued

| Time | Visual Observation of Disintegration at Star Pattern Debossing(s) | Visual Observation of Disintegration at remaining coating portions(s)* |
|---|---|---|
| 30 sec | Some observed; amount released progressively increasing | Some observed in other area ("500" number in center); amount released progressively increasing |

As can be seen from the results in Table 5, onset of disintegration from the spoke portions of the tablet occurred more rapidly than onset of disintegration from any other portion of the tablet.

The invention claimed is:

1. A dosage form comprising:
   a) a core having an exterior surface and first and second ends;
   b) at least one debossed pattern in said core;
   wherein said at least one debossed pattern contains at least one wall;
   wherein the at least one wall contains a wall angle from vertical of about 25 degrees or less; and
   c) a coating over portions of the exterior surface of the core.

2. The dosage form of claim 1, wherein the at least one debossed pattern contains a depth of more than about 0.25 mm.

3. The dosage form of claim 1, wherein the coating is a film-based coating.

4. The dosage form of claim 3, wherein the film-based coating comprises hydroxypropylmethylcellulose.

5. The dosage form of claim 1, comprising at least two debossed patterns in said core.

6. The dosage form of claim 1, wherein the core is a compressed tablet.

7. The dosage form of claim 6, wherein the compressed tablet has an elongated shape.

8. The dosage form of claim 1, wherein the core comprises at least one active ingredient and wherein the dosage form allows for dissolution of the at least one active ingredient following an immediate release profile.

9. The dosage form of claim 8, wherein the at least one active ingredient is selected from the group consisting of acetaminophen, acetyl salicylic acid, ibuprofen, naproxen, ketoprofen, flurbiprofen, diclofenac, cyclobenzaprine, pseudoephedrine, phenylephrine, phenylpropanolamine, chlorpheniramine, dextromethorphan, diphenhydramine, astemizole, terfenadine, fexofenadine, loratadine, desloratadine, cetirizine, and pharmaceutically acceptable salts, esters, and isomers thereof.

10. The dosage form of claim 1, wherein the coating is less than or equal to about 5% by weight as compared to a weight of the dosage form.

11. The dosage form of claim 9, wherein coating weight gain is less than or equal to about 3%.

12. A method for producing a dosage form comprising:
    a) debossing at least one pattern on a core, wherein said at least one debossed pattern contains at least one wall, and wherein the at least one wall contains a wall angle from vertical of about 25 degrees or less; and
    b) coating said core with a coating material.

13. The method of claim 12, wherein the dosage form is an elongated tablet.

14. The method of claim 12, wherein the coating near the at least one debossed pattern disintegrates at a faster rate than the coating on the remaining surface face of the tablet.

15. The method of claim 12, wherein a thickness of the coating in the at least one pattern is at least 10% lower than a thickness of the coating on a remainder of said tablet.

16. The dosage form of claim 5, wherein the at least two debossed patterns intersect.

* * * * *